(12) United States Patent
Gavney, Jr. et al.

(10) Patent No.: US 8,276,231 B2
(45) Date of Patent: Oct. 2, 2012

(54) ORAL-CARE DEVICE AND SYSTEM (76) Inventors: James A. Gavney, Jr., Palo Alto, CA (US); Jerry Mix, Redwood City, CA (US); Dennis Boyle, Palo Alto, CA (US); Rickson Sun, Palo Alto, CA (US); Christopher Loew, Palo Alto, CA (US); Pascal Homero Soboll, London (GB); Daniel Sung-hwe Kim, Mountain View, CA (US)

( * ) Notice: Subject to any disclaimer, the term of this patent is extended or adjusted under 35 U.S.C. 154(b) by 0 days.

(21) Appl. No.: 11/296,892

(22) Filed: Dec. 7, 2005

(65) Prior Publication Data

US 2006/0117506 A1 Jun. 8, 2006

Related U.S. Application Data (60) Division of application No. 10/692,837, filed on Oct. 24, 2003, now Pat. No. 7,181,799, which is a continuation-in-part of application No. 10/382,559, filed on Mar. 5, 2003, now Pat. No. 6,820,299, which is a continuation of application No. 09/588,686, filed on Jun. 5, 2000, now Pat. No. 6,571,417, which is a continuation-in-part of application No. 09/330,704, filed on Jun. 11, 1999, now Pat. No. 6,319,332.

(51) Int. Cl.
*A46B 9/04* (2006.01)
*A46B 13/02* (2006.01)
*A47L 13/11* (2006.01)

(52) U.S. Cl. .............. 15/22.1; 15/28; 15/97.1; 15/110; 15/114; 15/117; 15/167.1; 15/245

(58) Field of Classification Search ............... 15/22.1, 15/28, 97.1, 110, 114, 117, 167.1, 245
See application file for complete search history.

(56) References Cited

U.S. PATENT DOCUMENTS

| | | | |
|---|---|---|---|
| 1,128,139 | A | 2/1915 | Hoffman |
| 1,142,698 | A | 6/1915 | Grove et al. |
| 1,188,823 | A | 6/1916 | Plank |
| 1,191,556 | A | 7/1916 | Blake |

(Continued)

FOREIGN PATENT DOCUMENTS

CH    172320    12/1934

(Continued)

OTHER PUBLICATIONS

"A new high-performance manual toothbrush" Supported by the Colgate-Palmolive Company, 2004 Medical World Business Press, Inc.

(Continued)

*Primary Examiner* — Randall Chin
(74) *Attorney, Agent, or Firm* — James A. Gavney, Jr.; Jag Patent Services LLP (57) ABSTRACT A device with two or more regions configured to clean or treat a working surface is disclosed. Preferably, the device is an oral-care device with a power cleaning head. The power cleaning head comprises two or more regions, wherein at least one of the regions is configured to move and wherein at least one of the regions comprises a squeegee element. Preferably, the regions are configured to independently rotate, oscillate, vibrate or otherwise move while cleaning teeth and gums and can each include bristles, nodules, squeegee elements, or any combination thereof.

9 Claims, 10 Drawing Sheets

U.S. PATENT DOCUMENTS

| | | |
|---|---|---|
| 1,268,544 A | 6/1918 | Cates |
| 1,297,272 A | 3/1919 | Strang et al. |
| 1,405,279 A | 1/1922 | Cassedy |
| 214,701 A | 4/1924 | Dessau |
| 1,500,274 A | 7/1924 | Scarling |
| 1,526,267 A | 2/1925 | Dessau |
| 1,578,074 A | 3/1926 | Chandler |
| 1,588,785 A | 6/1926 | Van Sant |
| 1,598,224 A | 8/1926 | Van Sant |
| 290,515 A | 5/1928 | Voltz et al. |
| 305,735 A | 2/1929 | Leeson et al. |
| 1,705,249 A | 3/1929 | Henry |
| 1,707,118 A | 3/1929 | Goldberg |
| 1,720,017 A | 7/1929 | Touchstone |
| 1,766,529 A | 6/1930 | Peirson |
| 1,833,555 A | 11/1931 | Bell et al. |
| 1,852,480 A | 4/1932 | Ruetz |
| 1,868,893 A | 7/1932 | Gentle |
| 1,910,414 A | 5/1933 | Varga |
| 1,924,152 A | 8/1933 | Coney et al. |
| 1,965,009 A | 7/1934 | Stevens |
| 1,993,662 A | 3/1935 | Green |
| 1,993,763 A | 3/1935 | Touchstone |
| 2,008,636 A | 7/1935 | Brynan |
| 2,042,239 A | 5/1936 | Planding |
| 2,059,914 A | 11/1936 | Rosenberg |
| 2,088,839 A | 8/1937 | Coney et al. |
| 2,117,174 A | 5/1938 | Jones |
| 2,129,082 A | 9/1938 | Byrer |
| 2,139,245 A | 12/1938 | Ogden |
| 2,144,408 A | 1/1939 | Holmes |
| 2,154,846 A | 4/1939 | Heymann et al. |
| 2,164,219 A | 6/1939 | McGerry |
| 2,219,753 A | 10/1940 | Seguin |
| 2,226,145 A | 12/1940 | Smith |
| 2,244,699 A | 6/1941 | Hosey |
| 2,279,355 A | 4/1942 | Wilensky |
| 2,312,828 A | 3/1943 | Adamsson |
| 2,321,333 A | 6/1943 | Terry |
| 2,334,796 A | 11/1943 | Steinmetz et al. |
| 2,443,461 A | 6/1948 | Kempster |
| 620,151 A | 3/1949 | Emsa-Works et al. |
| 2,516,491 A | 7/1950 | Swastek |
| 2,518,765 A | 8/1950 | Ecker |
| 2,534,086 A | 12/1950 | Vosbikian et al. |
| 2,545,814 A | 3/1951 | Kempster |
| 2,587,382 A | 2/1952 | Pyne |
| 2,637,870 A | 5/1953 | Cohen |
| 2,644,974 A | 7/1953 | Anderson |
| 2,702,914 A | 3/1955 | Kittle et al. |
| 2,715,745 A | 8/1955 | Jacobsen |
| 2,757,668 A | 8/1956 | Meyer-Saladin |
| 2,807,820 A | 10/1957 | Dinhofer |
| 2,815,601 A | 12/1957 | Hough, Jr. |
| 2,875,458 A | 3/1959 | Tsuda |
| 2,884,151 A | 4/1959 | Biederman |
| 2,946,072 A | 7/1960 | Filler et al. |
| 2,987,742 A | 6/1961 | Kittle et al. |
| 34,109 A | 1/1962 | Fenshaw et al. |
| 3,103,027 A | 9/1963 | Birch |
| 3,110,052 A | 11/1963 | Whitman |
| 3,133,546 A | 5/1964 | Dent |
| 3,181,193 A | 5/1965 | Nobles et al. |
| 3,195,537 A | 7/1965 | Blasi |
| 3,230,562 A | 1/1966 | Birch |
| 3,231,925 A | 2/1966 | Conder |
| 3,261,354 A | 7/1966 | Shpuntoff |
| 66,834 A | 7/1967 | Harlan |
| 3,359,588 A | 12/1967 | Kobler |
| 3,400,417 A | 9/1968 | Moret |
| 3,491,396 A | 1/1970 | Eannarino et al. |
| 104,886 A | 6/1970 | Rhodehamel |
| 3,553,759 A | 1/1971 | Kramer et al. |
| 3,563,233 A * | 2/1971 | Bodine ............... 601/72 |
| 3,570,726 A | 3/1971 | Pomodoro |
| 116,030 A | 6/1971 | Devines |
| 116,346 A | 6/1971 | O'Brian |
| 3,641,610 A | 2/1972 | Lewis, Jr. |
| 3,939,522 A | 2/1976 | Shimizu |
| 3,969,783 A | 7/1976 | Shipman |
| 3,977,084 A | 8/1976 | Sloan |
| 3,992,747 A | 11/1976 | Hufton |
| 4,090,647 A | 5/1978 | Dunning |
| 4,115,893 A | 9/1978 | Nakata et al. |
| 4,128,910 A | 12/1978 | Nakata et al. |
| 218,431 A | 8/1979 | Dunham |
| 4,167,794 A | 9/1979 | Pomeroy |
| 4,277,862 A | 7/1981 | Weideman |
| 4,288,883 A | 9/1981 | Dolinsky |
| 4,428,091 A | 1/1984 | Janssen |
| 4,458,374 A | 7/1984 | Hukuba |
| 4,573,920 A | 3/1986 | d'Argembeau |
| 4,585,416 A | 4/1986 | DeNiro et al. |
| 4,610,043 A | 9/1986 | Vezjak |
| 4,691,405 A | 9/1987 | Reed |
| 4,727,986 A | 3/1988 | Feldstein |
| 4,763,380 A | 8/1988 | Sandvick |
| 4,812,070 A | 3/1989 | Marty |
| 4,827,551 A | 5/1989 | Maser et al. |
| 4,866,806 A | 9/1989 | Bedford |
| 411,910 A | 10/1989 | Van Horne |
| 4,887,924 A | 12/1989 | Green |
| 4,913,133 A * | 4/1990 | Tichy ............... 601/80 |
| 4,929,180 A | 5/1990 | Moreschini |
| 5,005,246 A | 4/1991 | Yen-Hui |
| 5,032,082 A | 7/1991 | Herrera |
| 5,040,260 A | 8/1991 | Michaels |
| D326,019 S | 5/1992 | Spangler et al. |
| 5,211,494 A | 5/1993 | Baijnath |
| 5,226,197 A | 7/1993 | Nack et al. |
| 5,249,327 A | 10/1993 | Hing |
| 5,283,921 A | 2/1994 | Ng |
| 5,289,605 A * | 3/1994 | Armbruster ............... 15/97.1 |
| 5,335,389 A | 8/1994 | Curtis et al. |
| 5,341,537 A | 8/1994 | Curtis et al. |
| 5,429,678 A | 7/1995 | Fany |
| 5,438,726 A | 8/1995 | Leite |
| 5,491,863 A | 2/1996 | Dunn |
| 5,528,793 A | 6/1996 | Schbot |
| 5,535,474 A | 7/1996 | Salazar |
| 5,584,690 A | 12/1996 | Maassarani |
| 5,604,951 A | 2/1997 | Shipp |
| 5,615,449 A | 4/1997 | Sepke |
| 5,628,082 A | 5/1997 | Moskovich |
| 5,669,097 A | 9/1997 | Klinkhammer |
| 5,689,850 A | 11/1997 | Shekalim |
| 5,711,759 A | 1/1998 | Smith et al. |
| 5,735,011 A | 4/1998 | Asher |
| 5,799,353 A | 9/1998 | Oishi et al. |
| 5,802,656 A | 9/1998 | Dawson et al. |
| 5,806,127 A | 9/1998 | Samoil et al. |
| 5,810,856 A | 9/1998 | Tveras |
| 5,839,149 A | 11/1998 | Scheier et al. |
| D402,116 S | 12/1998 | Magloff et al. |
| D403,510 S | 1/1999 | Menke et al. |
| 5,896,614 A | 4/1999 | Flewitt |
| 5,930,860 A | 8/1999 | Shipp |
| 5,966,771 A | 10/1999 | Stroud |
| 5,970,564 A | 10/1999 | Inns et al. |
| 5,980,542 A | 11/1999 | Saldivar |
| 5,991,959 A | 11/1999 | Raven et al. |
| 6,000,088 A | 12/1999 | Wright et al. |
| 6,003,187 A | 12/1999 | Footer et al. |
| 6,021,541 A | 2/2000 | Mori et al. |
| 6,032,313 A | 3/2000 | Tsang |
| 6,032,322 A | 3/2000 | Forsline |
| 6,041,467 A | 3/2000 | Roberts et al. |
| D422,143 S | 4/2000 | Beals et al. |
| 6,044,514 A | 4/2000 | Kaneda et al. |
| D424,808 S | 5/2000 | Beals et al. |
| D425,306 S | 5/2000 | Beals et al. |
| 6,065,890 A | 5/2000 | Weitz |
| 6,067,684 A | 5/2000 | Kweon |
| 6,077,360 A | 6/2000 | Takashima |
| 6,088,869 A | 7/2000 | Kaneda et al. |
| 6,092,255 A | 7/2000 | Kim |
| 6,099,309 A | 8/2000 | Cardarelli |

| | | |
|---|---|---|
| 6,108,854 A | 8/2000 | Dingert |
| 6,115,871 A | 9/2000 | Royer |
| 6,126,533 A | 10/2000 | Johnson et al. |
| 6,151,745 A | 11/2000 | Roberts et al. |
| 6,151,746 A | 11/2000 | Lewis, Jr. |
| 6,168,434 B1 | 1/2001 | Bohm-Van Diggelen |
| 6,182,323 B1 | 2/2001 | Bahten |
| 6,182,365 B1 | 2/2001 | Tseng et al. |
| 6,190,367 B1 | 2/2001 | Hall |
| 6,219,874 B1 | 4/2001 | van Gelder et al. |
| 6,240,590 B1 | 6/2001 | Nesbit |
| 6,245,032 B1 | 6/2001 | Sauer et al. |
| 6,254,390 B1 | 7/2001 | Wagner |
| 6,272,713 B1 | 8/2001 | Lotwin |
| 6,276,021 B1 | 8/2001 | Hohlbein |
| 6,299,508 B1 | 10/2001 | Gagliardi et al. |
| 6,311,358 B1 | 11/2001 | Soetewey et al. |
| 6,311,360 B1 | 11/2001 | Lanvers |
| 6,314,605 B1 | 11/2001 | Solanki et al. |
| 6,319,332 B1 | 11/2001 | Gavney, Jr. et al. |
| 6,349,442 B1 | 2/2002 | Cohen et al. |
| 6,421,867 B1 * | 7/2002 | Weihrauch .................. 15/28 |
| 6,446,295 B1 | 9/2002 | Calabrese |
| 6,463,619 B2 | 10/2002 | Gavney, Jr. |
| 6,510,575 B2 | 1/2003 | Calabrese |
| 6,513,182 B1 | 2/2003 | Calabrese et al. |
| 6,553,604 B1 | 4/2003 | Braun et al. |
| 6,571,417 B1 | 6/2003 | Gavney, Jr. et al. |
| 6,599,048 B2 | 7/2003 | Kuo |
| 742,639 A1 | 10/2003 | Harlan |
| 6,643,886 B2 | 11/2003 | Moskovich et al. |
| 6,647,585 B1 | 11/2003 | Robinson |
| D483,184 S | 12/2003 | Geiberger et al. |
| 6,658,688 B2 | 12/2003 | Gavney, Jr. |
| 6,658,692 B2 | 12/2003 | Lenkiewicz et al. |
| 6,668,418 B2 | 12/2003 | Bastien |
| 6,725,493 B2 | 4/2004 | Calabrese et al. |
| 6,751,823 B2 | 6/2004 | Biro et al. |
| 6,813,793 B2 | 11/2004 | Eliav et al. |
| 6,817,054 B2 | 11/2004 | Moskovich et al. |
| 6,820,299 B2 | 11/2004 | Gavney, Jr. |
| 6,820,300 B2 | 11/2004 | Gavney, Jr. |
| 6,859,969 B2 | 3/2005 | Gavney, Jr. |
| 6,865,767 B1 | 3/2005 | Gavney, Jr. |
| 6,886,207 B1 | 5/2005 | Solanki |
| 6,892,412 B2 | 5/2005 | Gatzemeyer et al. |
| 6,938,293 B2 | 9/2005 | Eliav et al. |
| 6,983,507 B2 | 1/2006 | McDougall |
| 907,842 A1 | 12/2008 | Meuzies |
| 915,251 A1 | 3/2009 | Vanderslice |
| 7,934,284 B2 * | 5/2011 | Braun et al. .................. 15/22.1 |
| 7,941,886 B2 * | 5/2011 | Chenvainu et al. ........... 15/22.4 |
| 1,006,630 A1 | 10/2011 | Clarke |
| 2001/0020314 A1 | 9/2001 | Calabrese |
| 2001/0039689 A1 | 11/2001 | Gavney, Jr. |
| 2002/0124337 A1 | 9/2002 | Calabrese et al. |
| 2003/0033680 A1 | 2/2003 | Davies et al. |
| 2003/0033682 A1 | 2/2003 | Davies et al. |
| 2003/0182746 A1 | 10/2003 | Fattori et al. |
| 2003/0196283 A1 | 10/2003 | Eliav et al. |
| 2004/0010869 A1 | 1/2004 | Fattori et al. |
| 2004/0045105 A1 | 3/2004 | Eliav et al. |
| 2004/0060132 A1 | 4/2004 | Gatzemeyer et al. |
| 2004/0060133 A1 | 4/2004 | Eliav |
| 2004/0060134 A1 | 4/2004 | Eliav et al. |
| 2004/0060135 A1 | 4/2004 | Gatzemeyer et al. |
| 2004/0060136 A1 | 4/2004 | Gatzemeyer et al. |
| 2004/0060137 A1 | 4/2004 | Eliav |
| 2004/0154112 A1 | 8/2004 | Braun et al. |
| 2004/0200016 A1 | 10/2004 | Chan et al. |
| 2005/0000048 A1 | 1/2005 | Hohlbein |
| 2005/0015907 A1 | 1/2005 | Georgi et al. |
| 2005/0049155 A1 | 3/2005 | Gavney et al. |
| 2005/0060822 A1 | 3/2005 | Chenvainu et al. |
| 2005/0102780 A1 | 5/2005 | Hohlbein |
| 2005/0102783 A1 | 5/2005 | Hohlbein |
| 2005/0166342 A1 | 8/2005 | Hohlbein |

FOREIGN PATENT DOCUMENTS

| | | |
|---|---|---|
| DE | 31 14 507 A1 | 3/1983 |
| DE | 298 16 488 U1 | 1/1999 |
| DE | 199 57 639 A1 | 6/2001 |
| EP | 0 435 329 A2 | 9/1989 |
| EP | 0 360 766 A1 | 3/1990 |
| FR | 2 636 818 | 3/1990 |
| FR | 2 793 136 | 11/2000 |
| GB | 2 040 161 A | 8/1980 |
| GB | 2 214 420 A | 9/1989 |
| GB | 2 319 170 A | 5/1998 |
| GB | 2 371 217 A | 7/2002 |
| JP | 9-140456 | 3/1997 |
| WO | WO 96/15696 | 5/1996 |
| WO | WO 96/20654 | 7/1996 |
| WO | WO 96/28994 | 9/1996 |
| WO | WO 97/16995 | 5/1997 |
| WO | WO 98/18364 | 5/1998 |
| WO | WO 98/22000 | 5/1998 |
| WO | WO 99/37181 | 7/1999 |
| WO | WO 00/64307 | 8/2000 |
| WO | WO 00/49911 | 11/2000 |
| WO | WO 00/76369 A2 | 12/2000 |
| WO | WO 01/01817 A1 | 1/2001 |
| WO | WO 01/21036 A1 | 3/2001 |
| WO | WO 03/030680 A1 | 4/2003 |
| WO | WO 03/043459 A2 | 5/2003 |
| WO | WO 2004/041023 A2 | 5/2004 |
| WO | WO 2004/064573 A1 | 8/2004 |

OTHER PUBLICATIONS

The Gillette Company, 2004 Annual Report and 2005 Proxy Statement.

* cited by examiner

ORAL-CARE DEVICE AND SYSTEM

RELATED APPLICATIONS

This application is a Divisional application of the application Ser. No. 10/692,837, filed Oct. 24, 2003, and titled "ORAL-CARE SYSTEM AND DEVICE," now U.S. Pat. No. 7,181,799, which is a Continuation-in-part of the application Ser. No. 10/382,559, filed Mar. 5, 2003, and titled "DENTITION CLEANING DEVICE AND SYSTEM," now U.S. Pat. No. 6,820,299, which is a continuation application of the application Ser. No. 09/588,686, filed Jun. 5, 2000, and titled "DENTITION CLEANING DEVICE AND SYSTEM," now U.S. Pat. No. 6,571,417, which is a Continuation-in-part of the application Ser. No. 09/330,704 filed Jun. 11, 1999, and titled "SQUEEGEE DEVICE AND SYSTEM", now U.S. Pat. No. 6,319,332. The application Ser. No. 10/692,837, filed Oct. 24, 2003, and titled "ORAL-CARE SYSTEM AND DEVICE, now U.S. Pat. No. 7,181,799 the application Ser. No. 10/382,559, filed Mar. 5, 2003, and titled "DENTITION CLEANING DEVICE AND SYSTEM, now U.S. Pat. No. 6,820,299, the application Ser. No. 09/588,686, filed Jun. 5, 2000, and titled "DENTITION CLEANING DEVICE AND SYSTEM," now U.S. Pat. No. 6,571,417 and the application Ser. No. 09/330,704, filed Jun. 11, 1999, and titled "SQUEEGEE DEVICE AND SYSTEM", now U.S. Pat. No. 6,319,332, are all hereby incorporated by reference. This patent application also claims priority under 35 U.S.C. 119 (e) of the co-pending U.S. Provisional Patent Application Ser. No. 60/439,317, filed Jan. 10, 2003, and titled "TOOTHBRUSH" and the co-pending U.S. Provisional Patent Application Ser. No. 60/463,347, filed Apr. 15, 2003, and titled "SQUEEGEE TOOTHBRUSH." The U.S. Provisional Patent Application Ser. No. 60/439,317 filed Jan. 10, 2003, and titled "TOOTHBRUSH" and the U.S. Provisional Patent Application Ser. No. 60/463,347, filed Apr. 15, 2003, and titled "SQUEEGEE TOOTHBRUSH" are also both hereby incorporated by reference.

FIELD OF THE INVENTION

This invention relates generally to cleaning and applicator devices. More specifically, this invention relates to cleaning and applicator devices with multiple regions configured to move independently.

BACKGROUND

Treating surfaces is an activity that occupies a considerable portion of most peoples time. For example, household surfaces are regularly cleaned and polished and/or require the application of treatment or cleaning materials to the household surfaces. Also, many industrial processes, such as cleaning floors and polishing wafers, require contacting surfaces to clean the surfaces and/or apply materials to the surfaces. Likewise, there are a number of medical and/or personal hygiene activities that require treating surfaces with contact elements to treat or clean the surfaces. A particular example is oral-care, which requires very specialized treatment of a surface in cleaning teeth and gums.

There are a number of different systems and devices available for cleaning teeth and gums. A number of these available systems and devices are inefficient at cleaning teeth and gums and require multiple pass scrubbing with oral cleaning agents, such as tooth pastes or gels, to effectively clean the teeth and gums. Typically, toothbrushes, for example, do not efficiently apply the oral cleaning agents to the teeth and gums and can be abrasive, causing loss of healthy gum tissue and/or damage to teeth. Further, toothbrushes can require a high degree of technique and/or dexterity to be used effectively for cleaning teeth and gums.

What is needed is a dentition cleaning system and device that can efficiently apply oral cleaning agents to teeth and gums and that can clean teeth and gums without a high degree of technique or dexterity. Further, what is needed is a dentition cleaning system and device that is less abrasive to teeth and gums than a conventional bristle toothbrush.

SUMMARY OF THE INVENTION

The present invention is directed to a device comprising a head that is configured to clean surfaces, treat surfaces and/or apply materials to surfaces. Preferably, the head is a cleaning head that is configured to clean and/or treat teeth and gums. However, it will be clear to one skilled in the art that the present invention can equally be applied to devices that are configured to clean any number of different surfaces including, but not limited to, floors, cars, wafers and/or appliances.

In accordance with the present invention, a device comprises a cleaning head with two or more regions, wherein at least one of the regions preferably comprises a squeegee element configured to treat a working surface and at least one of the regions comprises bristles. In accordance with a preferred embodiment of the invention, at least one of the regions is configured to move independently of another of the regions. To move independently, herein, means that one of the regions is stationary while another region moves or that the regions move separately from one or more of the other, but does not necessarily mean that the regions are not synchronized to move with a similar or the same motion or that the regions are not coupled to the same mechanism to drive the motion of the regions. Preferably, one or more of the regions are configured to vibrate, rotate, oscillate or otherwise automatically move relative to and independently from another of the regions. In accordance with further embodiments of the invention two or more of the regions comprises bristle and squeegee elements. In still further embodiments of the invention, one or more of the regions of the cleaning head comprises nodules, i.e., resilient protrusions with any number of different geometries such as described below and further described in U.S. patent application Ser. No. 09/957,302, filed Sep. 19, 2001, now U.S. Pat. No. 6,865,767, and titled "DEVICE WITH MULTI-STRUCTURAL CONTACT ELEMENTS," the contents of which are hereby incorporated by reference.

The squeegee elements utilized in the present invention can have any number of different geometries including curved, rounded angled, corrugated, pointed and/or textured walls and/or wiping edges. Squeegee elements can include squeegee segments with one or more terminus ends and/or squeegee segments that form matrices of squeegee compartments and continuous squeegee segments that encircle portions of regions. Squeegees utilized in the present invention can be formed from any number of different materials, but are preferably formed from a resilient polymeric material such as silicon, latex, rubber, polyurethane or a combination thereof. Preferably, squeegees, or a portion thereof, are formed from a material, or materials, that can be molded and that result in squeegee elements with hardness values in a range of 10 to 100 Shores A, as defined in the D2240-00 Standard Test Method for Rubber Property-Durometer Hardness, published by the American Society for Testing Materials, the contents of which are hereby incorporated by reference. Additional details of squeegee configurations are provided in the U.S. Pat. No. 6,319,332, titled "SQUEEGEE DEVICE AND SYS- TEM," and U.S. Pat. No. 6,571,417, titled "DENTITION CLEANING DEVICE AND SYSTEM," the contents of which are also both hereby incorporated by reference.

Squeegees, in accordance with still further embodiments of the present invention, include an abrasive material that is integrated with the material(s) used to form the squeegees and/or are applied to surfaces of squeegee walls and/or edges after they are formed. Methods and materials for making molded abrasive structures are described in U.S. Pat. No. 6,126,533, and titled "MOLDED ABRASIVE BRUSH", the contents of which are hereby incorporated by reference.

In accordance with a preferred embodiment of the invention, a squeegee element comprises an elongated squeegee segments with smaller fins that protrude from walls of the elongated squeegee segment and provide top wiping edges and side wiping edges, such as described in detail in U.S. patent application Ser. No. 10/454,281, filed Jun. 3, 2003, entitled "MULTI-DIRECTIONAL WIPING ELEMENTS AND DEVICES USING THE SAME", now U.S. Pat. No. 6,859,969, the contents of which are hereby incorporated by reference.

In accordance with further embodiments of the invention, a system or device comprises a handle which provides power to a motorized cleaning head comprising the regions, such as described above. The cleaning head can be configured to detachably couple to the handle or, alternatively, can be permanently attached to the handle. In accordance with further embodiments of the invention, one or more of the regions can be configured to detachably couple to a support structure of the cleaning head, such that regions, wiping elements, bristles or combinations thereof can be replaced when they are worn out. It will be understood that the handle and/or the cleaning head are configured with any number of moving parts, such as gears, which allow a first region and/or a second region to move independently, such as described above. The handle can include a battery or battery pack that can be recharged by docking to a recharging station. The handle can also include a motor and/or other mechanisms for driving the moving action of one or more of the regions either by battery or by plugging the device into a power source, such as an electrical power outlet.

In accordance with a further embodiment of the present invention, a first region comprising bristles, squeegee elements and/or nodules encircles a second region comprising bristles, squeegee elements and/or nodules, wherein one or both of the first region and the second region are configured to move. For example, the first region is configured to rotate or oscillate relative to the second region and/or the second region is configured to rotate or oscillate in an opposite direction at the same or at a faster rate.

For clarity, devices have been described below with a first region and a second region. However, it will be clear to one skilled in the art, that systems and devices of the present invention can be configured with any number of regions each with contact elements (e.g., squeegees, bristles and nodules), wherein one or more of the regions are configured to move independently from one or more of the other regions. Devices, in accordance with further embodiment of the invention, are configured with apertures to dispense materials onto a working surface and/or remove materials from the working surface, such as those described in U.S. Pat. Nos. 6,319,332 and 6,571,417, referenced previously.

DETAILED DESCRIPTION

Figure 1A:
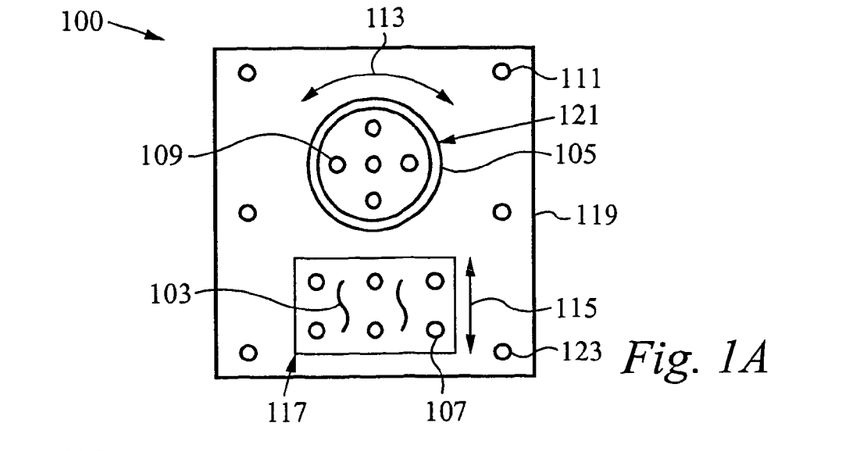
FIGS. 1A-C show cleaning heads with independently movable regions, in accordance with the embodiments of the invention.

FIG. 1A shows a schematic top view of a cleaning head configuration 100, in accordance with the embodiments of the invention. The cleaning head configuration 100 comprises a first region 121 and a second region 117 that are configured to move independently from each other. In accordance with the embodiments of the invention, the first region 121 comprises a continuous squeegee element 105 that encircles a portion of the first region 121 and bristles, bristle tufts and/or nodules 109 protruding therefrom. While FIGS. 1A-C are described as having bristles or bristle tuft, it will be clear to one skilled in the art and from the description below that the cleaning head configuration can include, in place of bristle or bristle tufts or in addition to bristles or bristle tufts, nodules such as those described with reference to FIGS. 6A-H and FIGS. 7A-G below.

Still referring to FIG. 1A, the first region 121 is preferably configured to rotate and/or oscillate, as indicated by the arrow 113, independently from the second region 117, which can be stationary or configured to move, for example in a backward and forward motion as indicated by the arrow 115. The second region 117 preferably comprises bristle, bristle tufts and/or nodules 107 that protrude therefrom and can also include one or more curved squeegee elements or wave-shaped squeegee elements 103. The cleaning head configuration 100 includes a support structure 119 with bristle, bristle tufts and/or nodules 111 and 123 protruding therefrom.

Figure 1B:
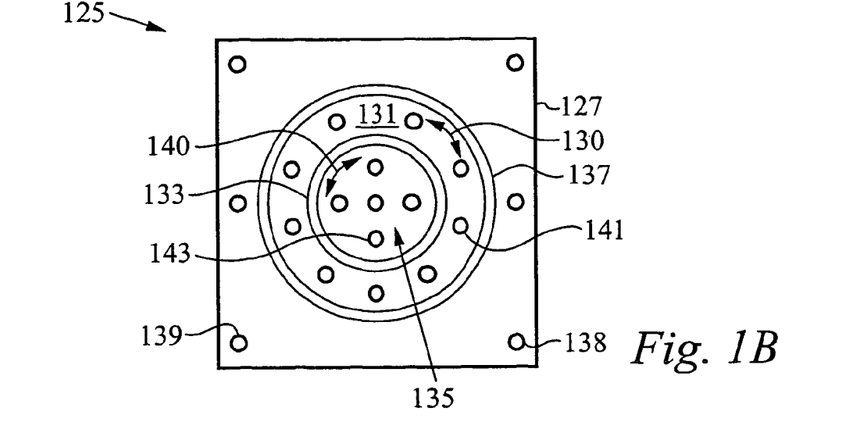
Figure 1C:
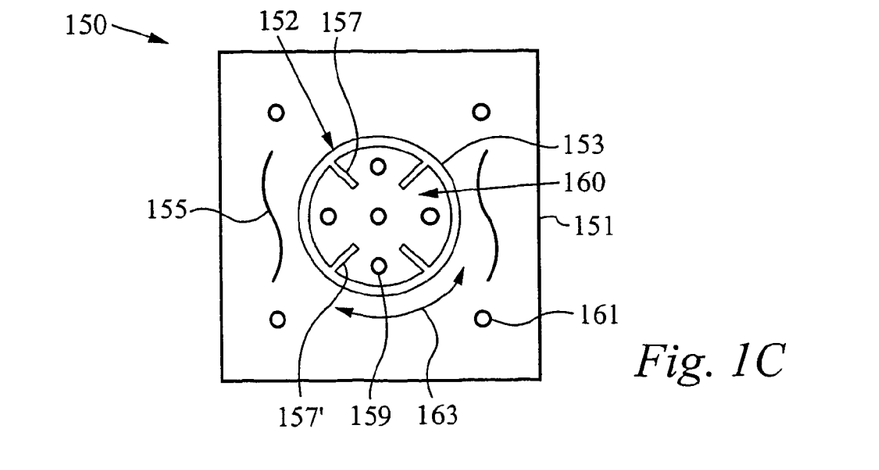

FIG. 1B, shows a schematic top view of a cleaning head configuration 125, in accordance with further embodiments of the invention. The cleaning head configuration 125 comprises a first region 131 and a second region 135 that are configured to move independently from each other. In accordance with this embodiment, the first region 131 comprises a first continuous squeegee 137 that encircles a first set of bristles and/or nodules 141 protruding from the first region 131 and encircles the second region 135. The second region 135 comprises a second continuous squeegee 133 that encircles a second set of bristles and/or nodules 143 protruding from the second region 135. Accordingly, first region 131 can be described as surrounding the second region 135.

Still referring to FIG. 1B, the first region 131 and the second region 135 are preferably configured to rotate and/or oscillate as indicated by the arrows 130 and 140, respectively. In accordance with a preferred embodiment of the invention, the first region 131 and the second region 135 are configured to move in opposite directions while rotating and/or oscillating. It will be clear to one skilled in the art that the first region 131 and the second region 135 can be configured to move in the same direction at the same or at a different rate of rotation and/or oscillation. In accordance with the invention, the cleaning head configuration 125 can also have support structure 127 with bristle, bristle tufts and/or nodules 138 and 139 protruding therefrom.

FIG. 1C, shows a schematic top view of a cleaning head configuration 150 in accordance with yet further embodiments of the invention. The cleaning head configuration 150 comprises at least one region 160 that is configured to rotate, oscillate and/or otherwise move in one or more directions, as indicated by the arrow 163. The region 160 preferably includes one or more squeegee elements 152. In accordance with the embodiments of the invention, the squeegee element 152 comprises a primary squeegee segment 153 with squeegee wiping fins 157 and 157' that protrude from an inner wall of the primary squeegee segment 153.

Still referring to FIG. 1C, the primary squeegee segment 153, in accordance the embodiments of the invention, is a continuous segment 153 that encircles at least a portion of the region 160 and bristles, bristle tufts and/or nodules 159 protruding from the encircled portion of the region 160. While the squeegee wiping fins 157 and 157' are shown here as protruding from an inner wall of the continuous primary squeegee segment 153, it will be clear to one skilled in the art that in addition to the squeegee wiping fins 157 and 157' or alternatively to the squeegee wiping fins 157 and 157', the squeegee element 152 can include one or more squeegee wiping fins protruding from an outer wall of the continuous squeegee segment 153. Also, while the primary squeegee segment 153 is shown here as a continuous squeegee segment, any number of geometries are contemplated, such as those described with reference to FIGS. 4A-M below. Squeegee configurations can have squeegee wiping fins with contoured or shaped wiping edges and/or wiping walls. Also, squeegee wiping fins can have wiping edges that protrude to the same or different heights than the wiping edges of a primary squeegee segment to which they are attached. A number of squeegee element configurations that have squeegee wiping fins are described in U.S. patent application Ser. No. 10/454,281, filed Jun. 3, 2003, and titled "MULTI-DIRECTIONAL WIPING ELEMENTS AND DEVICES USING THE SAME," now U.S. Pat. No. 6,859,969, referenced previously.

Figure 2:
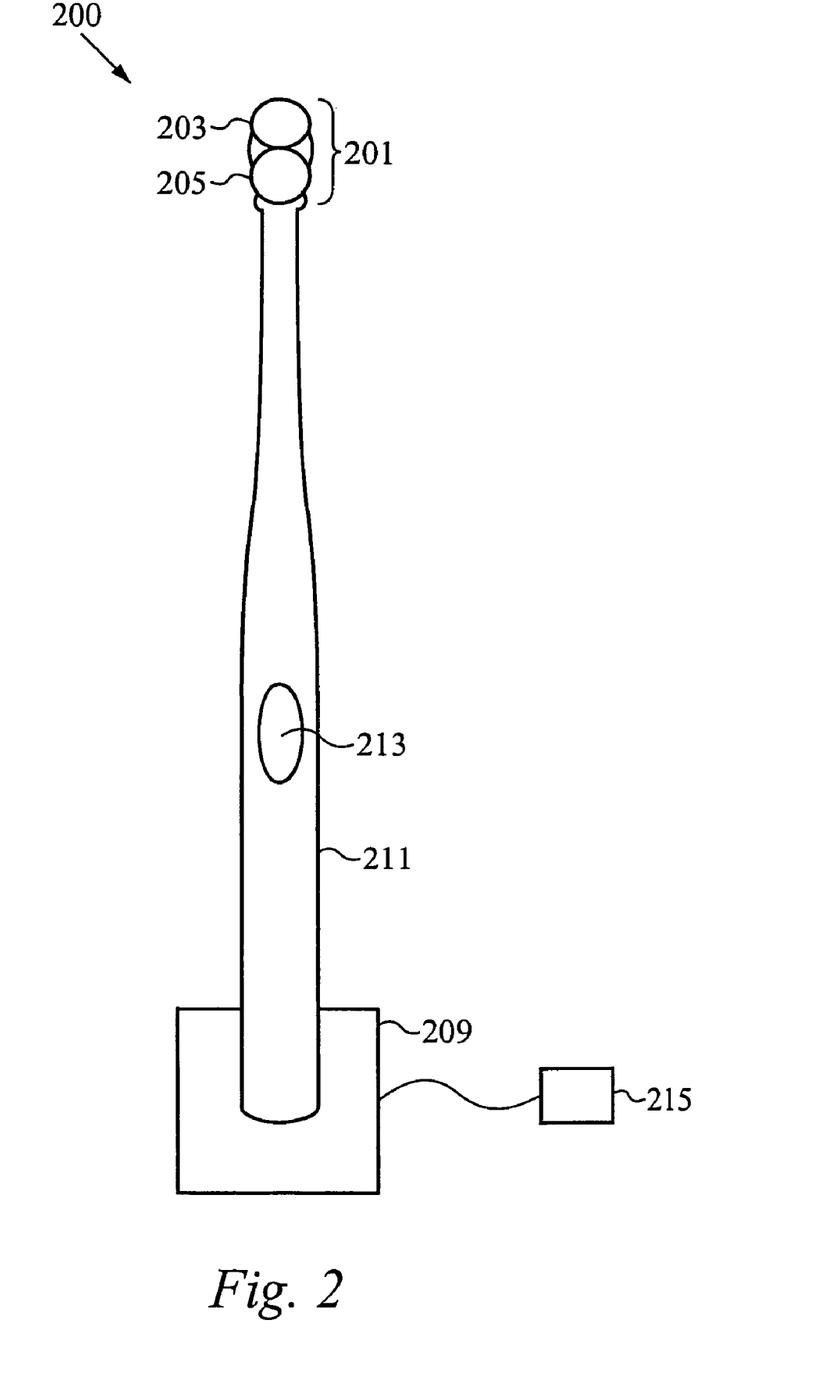
FIG. 2 shows an electric powered oral-care device comprising a power cleaning head with independently movable regions, in accordance with the embodiments of the invention.

FIG. 2 shows an electric powered oral-care apparatus 200 comprising a power cleaning head 201 with independently movable regions 203 and 205 such as described with reference to FIGS. 1A-C above and FIGS. 3A-C below. In accordance with the embodiments of the invention, the electric powered oral-care apparatus 200 comprises a power or recharging station 209 for docking a body portion 211 of the oral-care apparatus 200. The power or recharging station 209 comprises means 215 for plugging the power or recharging station 209 into an electrical receptacle and recharging a battery (not shown) housed within the body portion 211 of the oral-care apparatus 200, wherein the battery is configured for providing power to a driver mechanism (not shown) that moves one or both of the regions 203 and 205. Alternatively, or in addition to the power supply mechanism described above, the apparatus 200 can be configured to be powered with disposable batteries (not shown) that are housed in the body portion 211 of the oral-care apparatus 200. Preferably, the oral-care apparatus 200 has a power switch 213 for energizing the power head 201 to move the power cleaning head 201 on or turn it off. Also, the oral-care apparatus 200 can include any number of timer mechanisms to indicate to a user a preferred amount of time to clean teeth and gums with the oral-care apparatus 200. For example, the oral-care apparatus 200 can be configured to automatically shut off in a predetermined period of time after being energized with the power switch 213.

Figure 3A:
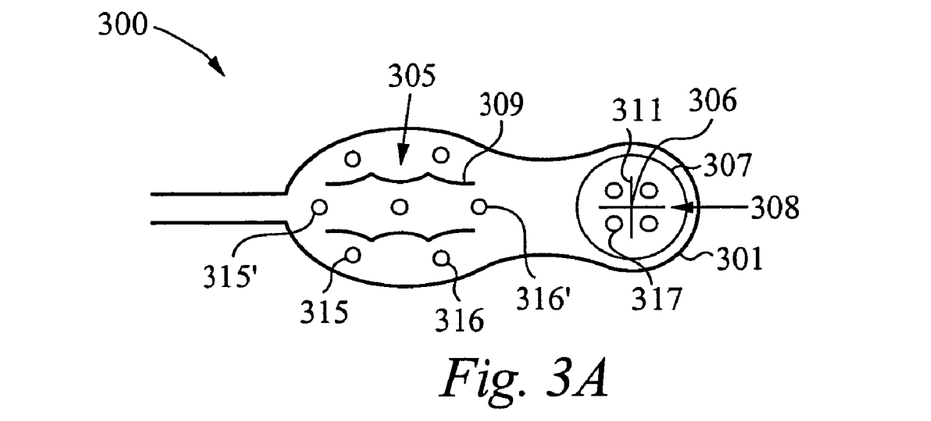
FIGS. 3A-C show oral-care cleaning heads with movable regions comprising squeegee elements, bristles and/or nodules in accordance with the embodiments of the invention.
Figure 3B:
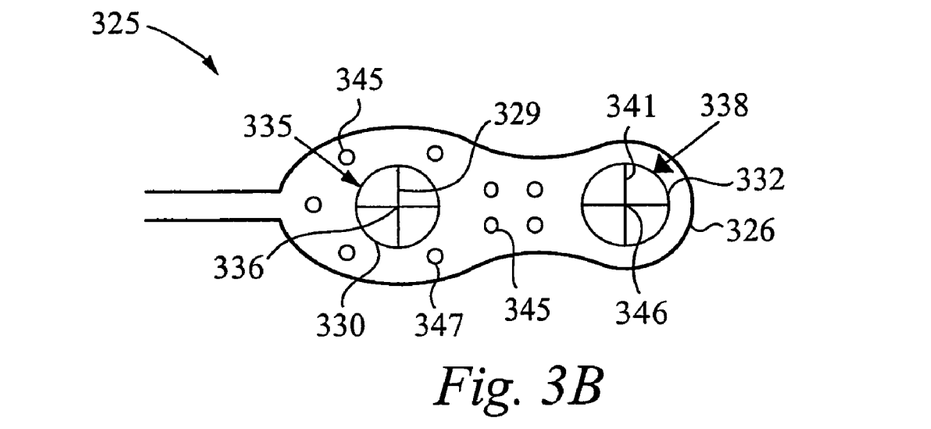
Figure 3C:
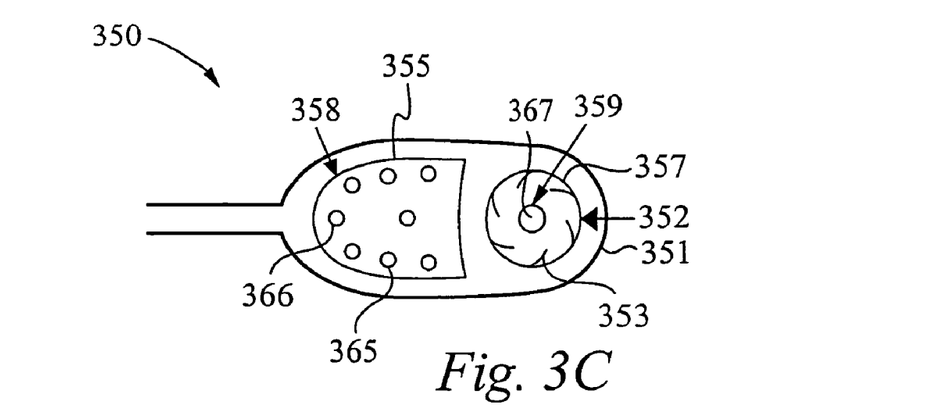

FIGS. 3A-C show oral-care cleaning heads 300, 325 and 350 with movable regions comprising squeegee elements, bristles, nodules and/or combinations thereof, in accordance with the embodiments of the invention. Referring now to FIG. 3A, the oral-care cleaning head 300 comprises a base structure 301 for supporting a first region 305 and a second region 307. The first region 305 comprises one or more squeegee elements 309 protruding therefrom. The squeegee elements 309 are shown here as wave-like, wherein the squeegee elements 309 have curved squeegee walls that extend in a number of directions two or more times (i.e., wave-like). While the squeegee elements 309 are shown with curved or wave-like walls, squeegee elements with linear or straight squeegee walls are also contemplated. Also, as described above walls of the squeegee elements and/or the top wiping squeegee edges of the squeegee elements 309 can be contoured or shaped in any number of different ways. In addition to the squeegee elements 309, the first region 305 can also have one or more tufts of bristles 315 and 315' and/or nodules 316 and 316' protruding therefrom in directions that are the same or different from that of the squeegee element 309.

Still referring to FIG. 3A, the second region 308 of the oral-care cleaning head 300 can comprise a squeegee element 311 protruding therefrom. The squeegee element 311 can have any number of different geometries, but is shown here as a cross-shaped squeegee element 311, with a number of squeegee segments intersecting at a common position 306. The second region 308 of the oral-care cleaning head 300 can also comprise bristle tufts 317 and/or nodules protruding therefrom in directions that are the same or different from that of the squeegee element 311. Also, the second region 308 of the oral cleaning head 300 can comprise a continuous squeegee element 307 encircling a portion of the second region 308, such that the second region 308 is capable of cupping and holding an oral-care solution, paste and/or gel. In operation, the oral-care cleaning solution, paste and/or gel is applied to the oral-care cleaning head 300 and the second region 308 rotates, oscillates, vibrates and/or otherwise moves relative to the first region while cleaning teeth and/or gums.

Referring now to FIG. 3B, the oral-care cleaning head 325 comprises a base structure 326 for supporting a first region 335 and a second region 338. The first region 335 comprises a first squeegee element protruding therefrom. The first squeegee element is shown here having a cross-shaped squeegee segment 329 with a number of squeegee segments intersecting at a common position 336. Also, the first squeegee element can comprise a continuous squeegee wall segment 330 encircling a portion of the first region 335 and the cross-shaped squeegee segment 329, wherein the walls of the cross-shaped squeegee segment 329 intersect with the continuous squeegee wall segment 330 and wherein the first squeegee element is capable of cupping and holding an oral-care solution, paste and/or gel during a cleaning operation. Also, it is noted that the first region 335 can include one or more bristle tufts and/or nodules (not shown) protruding therefrom in directions that are the same or different from that of the first squeegee element.

Still referring to FIG. 3B, the oral-care cleaning head 325 comprises a second region 338 with a second squeegee element protruding therefrom. The second squeegee element is shown here having a cross-shaped squeegee segment 341 with a number squeegee segments intersecting at a common position 346 and a continuous squeegee wall segment 332 encircling a portion of the second region 338 and the cross-shaped squeegee segment 341. In accordance with the embodiments of the invention, the second region 338 can also include one or more bristle tufts and/or nodules (not shown) protruding therefrom and/or the oral-care cleaning head 325 can have one or more bristle tufts 345 protruding and/or nodules 347 protruding from the support structure 326 in directions that are the same or different from that of the first or second squeegee element. In operation, an oral-care cleaning solution, paste and/or gel is applied to the oral-care cleaning head 325, and the first region 335 and the second region 338 rotate, oscillate, vibrate and/or otherwise move independently of each other while cleaning teeth and/or gums. For example, the first region 335 can rotate or oscillate in one direction while the second region 338 can rotate or oscillate in an opposite direction. While the first squeegee element and the second squeegee element are shown here as combinations of cross-shaped segments 329 and 341 and surrounding continuous squeegee segments 330 and 332, respectively, any number of squeegee element geometries and shapes are contemplated including, but not limited to, those described with reference to FIGS. 4A-M.

Referring now to FIG. 3C, the oral-care cleaning head 350 comprises a support structure 351 for supporting a first region 358 and a second region 359. The first region 358 comprises bristles 365 and/or nodules 366 protruding therefrom. The second region 359 comprises a squeegee element 352. The squeegee element 352 preferably comprises a continuous squeegee wall segment 357 that encircles a portion of the second region 359 and squeegee fins 353. The squeegee fins 353 protrude from an inner wall of the continuous squeegee wall segment 357. The squeegee fins 353 can protrude from the continuous squeegee wall segment 357 at any angle suitable for the application at hand and can protrude to the same or a different height from the support structure 351 than the top wiping edges of the continuous squeegee wall segment 357. Squeegee elements with squeegee fins are further described in U.S. patent application Ser. No. 10/454,281, filed Jun. 3, 2003 and titled "MULTI-DIRECTIONAL WIPING ELEMENTS AND DEVICES USING THE SAME", now U.S. Pat. No. 6,859,969, referenced previously.

In operation, an oral-care cleaning solution, paste and/or gel is applied to the oral-care cleaning head 350 and the second region 359 rotates, oscillates, vibrates and/or otherwise moves independently of the first region 358 while cleaning teeth and/or gums. For example, the second region 359 can rotate or oscillate while the first region 358 moves in a back and forth motion and/or vibrates, such as described above with reference to FIGS. 1A-C.

Still referring to FIG. 3C, the oral-care cleaning head 350 can also include a continuous squeegee element 355 that surrounds a portion of the first region 358. Preferably, the second region 359 of the oral cleaning head 350 further comprises one or more bristle tufts or nodules 367 that are surrounded by the continuous squeegee wall segment 357 and that are configured to move along with the squeegee element 352. While the oral-care cleaning heads 300, 325 and 350 have been described as having squeegee elements, bristle, nodules and combinations thereof, it will be clear to one skilled in the art that bristles are not required.

FIGS. 4A-M illustrate top views of squeegee configurations, or portions thereof, in accordance with further embodiments of the invention, wherein intersecting squeegee segments have different lengths, the same lengths, different heights or the same heights to provide top wiping edges and side wiping edges. Squeegee configurations, or portions thereof, as described with reference to FIGS. 4A-M, can include bristles and/or nodules that protrude from a support surface to the same height or different heights as the squeegee wiping edges of the squeegee segments. Also, the squeegee configurations can include bristles and/or nodules that protrude from the support surface at the same angles or different angles from that of the squeegee segments relative to the support surface.

Figure 4A:
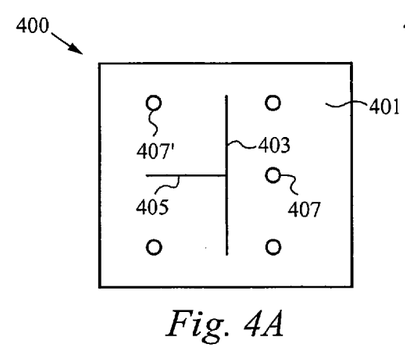
FIGS. 4A-M illustrate top views of portions of cleaning heads with squeegee elements, bristles and/or nodules, in accordance with the embodiments of the invention.

Referring now to FIG. 4A, a squeegee configuration 400, in accordance with the embodiments of the invention, comprises elongated squeegee segments 403 and 405 that intersect and provide top wiping edges and side wiping edges, as explained above. One, or both, of the elongated squeegee segments 403 and 405 protrude from a support surface 401 and can be surrounded or flanked by bristles and/or nodules 407 and 407' that also protrude from the support surface 401 and are preferably configured to wipe a working surface (not shown) simultaneously with the top wiping edges of the elongated squeegee segments 403 and 405.

Figure 4B:
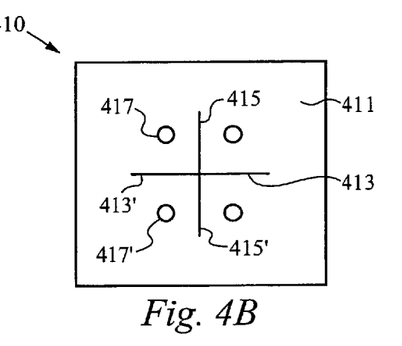

Referring now to FIG. 4B, a squeegee configuration 410, in accordance with the embodiments of the invention, comprises elongated squeegee segments 413, 413', 415 and 415' that intersect and provide top wiping edges that form a cross-shape with side wiping edges. One or more of the elongated squeegee segments 413, 413', 415 and 415' protrude from a support surface 411 and can be surrounded or flanked by bristles or nodules 417 and 417' that also protrude from the support surface 411 and are preferably configured to wipe a working surface (not shown) simultaneously with the top wiping edges of the elongated squeegee segments 413, 413', 415 and 415'.

Figure 4C:
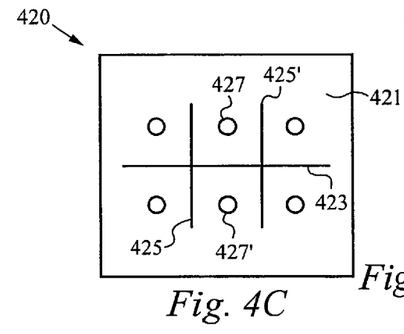

Referring now to FIG. 4C, a squeegee configuration 420, in accordance with the embodiments of the invention, comprises a major elongated squeegee segment 423 and a plurality of minor intersecting squeegee segments 425 and 425' that intersect with a wall of the major elongated squeegee segment 423 to provide cross-like top wiping edges and side wiping edges. One or more of the major squeegee segment 423 and the minor squeegee segments 425 and 425' protrude from a support surface 421 and can be surrounded or flanked by bristles and/or nodules 427 and 427' that also protrude from the support surface 421 and are preferably configured to wipe a working surface (not shown) simultaneously with the top wiping edges of the squeegee segments 423, 425 and 425'.

Figure 4D:
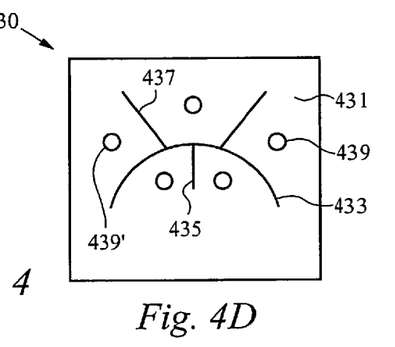

Referring now to FIG. 4D, a squeegee configuration 430, in accordance with the embodiments of the invention, comprises one or more curved squeegee segments 433 and a plurality intersecting squeegee segments 435 and 437. The intersecting squeegee segments 435 and 437 can extend from inside of the curvature of the squeegee segment 433, such as 435, or radiate outward from outside of the curvature of the squeegee segment 433, such as 437, to provide top wiping edges and side wiping edges. The curved squeegee segment 433 and the intersecting squeegee segments 435 and 437 protrude from a support surface 431 and can be surrounded or flanked by bristles and/or nodules 439 and 439' that also protrude from the support surface 431 and are preferably configured to wipe a working surface (not shown) simultaneously with the top wiping edges of the curved 433 and intersecting squeegee segments 435 and 437.

Figure 4E:
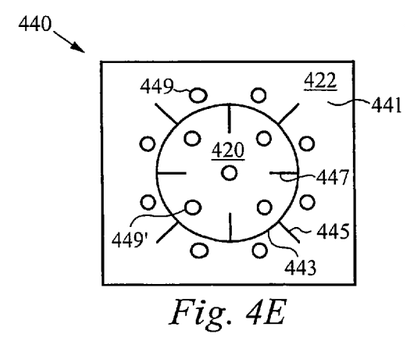

Referring now to FIG. 4E, a squeegee configuration 440, in accordance with the embodiments of the invention, comprises a curved and continuous squeegee segment 443 that forms or bounds an inner squeegee region 420 and an outer squeegee region 422. The squeegee configuration 440 can further comprise intersecting squeegee segments 447 that extend form an inside wall of the curved and continuous squeegee segment 443 and/or intersecting squeegee segments 445 that extend from an outer wall of the curved and continuous squeegee segment 443 to provide top wiping edges and side wiping edges. The curved and continuous squeegee segment 443 and the intersecting squeegee segments 445 and 447 protrude from a support surface 441 and can be surrounded or flanked by bristles and/or nodules 449 and 449' that also protrude from the support surface 441 and are preferably configured to wipe a working surface (not shown) simultaneously with the top wiping edges of the curved and continuous squeegee segment 443 and intersecting squeegee segments 445 and 447.

Figure 4F:
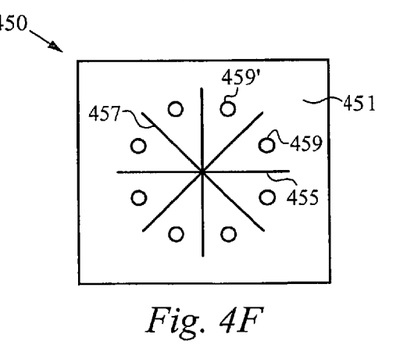

Referring now to FIG. 4F, a squeegee configuration 450, in accordance with the embodiments of the invention, comprises elongated squeegee segments 455 and 457 that intersect and extend at angles less than 90 degrees relative to each other and provide spoke-shaped top wiping edges and side wiping edges. The elongated squeegee segments 455 and 457 protrude from a support surface 451 and can be surrounded or flanked by bristles and/or nodules 459 and 459' that also protrude from the support surface 451 and are preferably configured to wipe a working surface (not shown) simultaneously with the top wiping edges of the elongated squeegee segments 455 and 457.

Figure 4G:
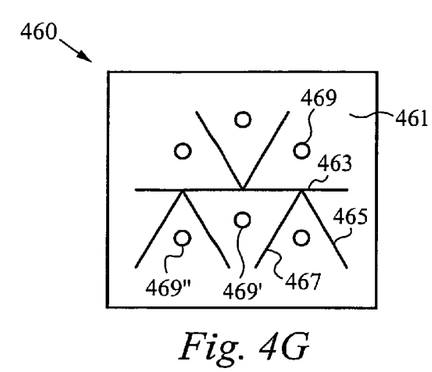

Referring now to FIG. 4G, a squeegee configuration 460, in accordance with the embodiments of the invention, comprises a major squeegee segment 463 and a plurality of minor and intersecting squeegee segments 465 and 467 that intersect a wall of the major squeegee segment 463 and extend from a wall of the major squeegee segment 463 at angles less than or greater than 90 degrees to provide top wiping edges and side wiping edges. The major squeegee segment 463 and the minor squeegee segments 465 and 467 can protrude from a support surface 461 and can be surrounded or flanked by bristles and/or nodules 469, 469' and 469" that also protrude from the support surface 461. The bristle or nodules 469, 469' and 469" are preferably configured to wipe a working surface (not shown) simultaneously with the top wiping edges of the squeegee segments 463, 465 and 467.

Figure 4H:
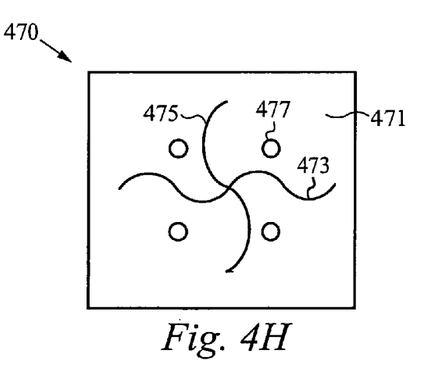

Referring now to FIG. 4H, a squeegee configuration 470, in accordance with the embodiments of the invention, comprises curved squeegee segments 473 and 475 that intersect and provide curved or wave-like top wiping edges and side wiping edges. One or more of the curved squeegee segments 473 and 475, or a portion thereof, protrude from a support surface 471 and can be surrounded or flanked by bristles and/or nodules 477 that also protrude from the support surface 471 and are preferably configured to wipe a working surface (not shown) simultaneously with the top wiping edges of the squeegee segments 473 and 475.

Figure 4I:
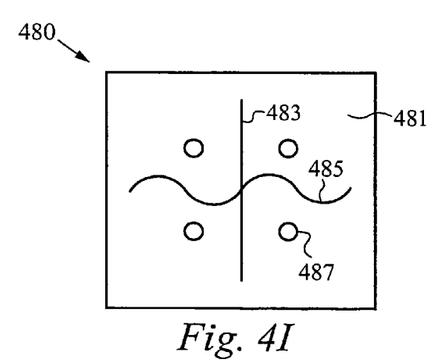

Referring now to FIG. 4I, a squeegee configuration 480, in accordance with the embodiments of the invention, comprises a linear squeegee segment 483 and a curved squeegee segment 485 that intersect and provide linear and curved top wiping edges and side wiping edges. One or more of the squeegee segments 483 and 485, or a portion thereof, protrude from a support surface 481 and can be surrounded or flanked by bristles and/or nodules 487 that also protrude from the support surface 481 and are preferably configured to wipe a working surface (not shown) simultaneously with the linear and curved top wiping edges of the squeegee segments 483 and 485.

Figure 4J:
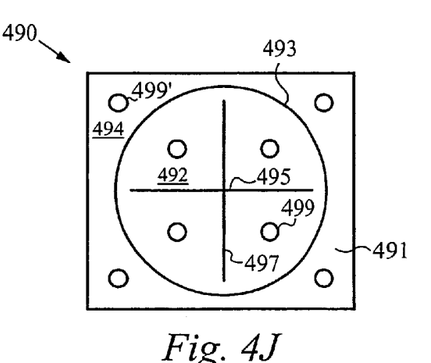

Referring now to FIG. 4J, a squeegee configuration 490, in accordance with the embodiments of the invention, comprises a continuous squeegee segment 493 that forms or bounds an inner squeegee region 492 and an outer squeegee region 494. The continuous squeegee segment 493 has a continuous top wiping edge that encircles or surrounds intersecting squeegee segments 495 and 497. The intersecting squeegee segments 495 and 497 provide cross-shaped top wiping edges and side wiping edges, as explained above. At least a portion of the continuous squeegee segment 493 and one or more of the intersecting squeegee segments 495 and 497 protrude from a support surface 491. Bristles and/or nodules can protrude from the support surface 491 corresponding to the inner squeegee region 492 (as with 499), the outer squeegee region 494 (as with 499') or both, such that the intersecting squeegee segments 495 and 497 and/or the continuous squeegee segment 493 are surrounded or flanked by bristles and/or nodules 499 and 499'. Preferably, the bristles and/or nodules 499 and 499' are configured to wipe a working surface (not shown) simultaneously with the top wiping edges of the squeegee segments 493, 495 and 497.

Figure 4K:
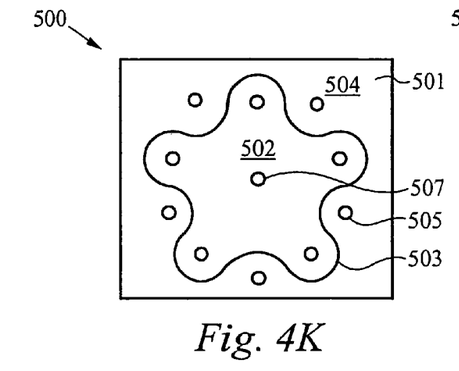

Referring now to FIG. 4K, a squeegee configuration 500, in accordance with the embodiments of the invention, comprises a continuous wave-shaped squeegee segment 503 that forms or bounds an inner squeegee region 502 and an outer squeegee region 504. The continuous wave-shaped squeegee segment 503 can be surrounded or flanked by bristle, bristle sections and/or nodules 505 and 507. Preferably, the bristle, bristle sections and/or nodules 505 and 507 are configured to move and contact a working surface (not shown) simultaneously with the top wiping edge of the continuous wave-shaped squeegee segment 503.

Figure 4L:
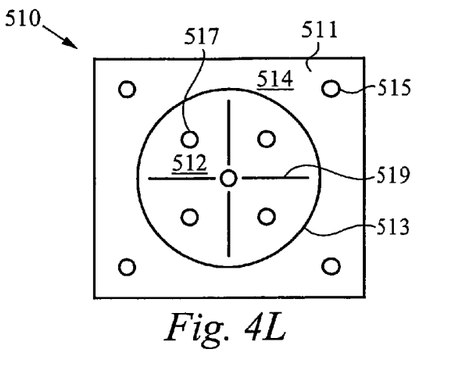

Referring now to FIG. 4L, a squeegee configuration 510, in accordance with the embodiments of the invention, comprises a continuous squeegee 513 that protrudes from a support surface 511 forms or bounds an inner squeegee region 512 and an outer squeegee region 514. The continuous squeegee can be surrounded or flanked by bristles, bristle sections and/or nodules 515 and 517. Preferably, the bristle, bristle sections and/or nodules 515 and 517 are configured to move and contact a working surface (not shown) simultaneously with the top wiping edge of the continuous squeegee 513. The squeegee configuration can also include squeegee segment 519 that protrudes from the inner squeegee region 512. Preferably, the bristles, bristle sections and/or nodules 515 and 517 are configured to wipe the working surface simultaneously with the top wiping edge of the continuous squeegee 513.

Figure 4M:
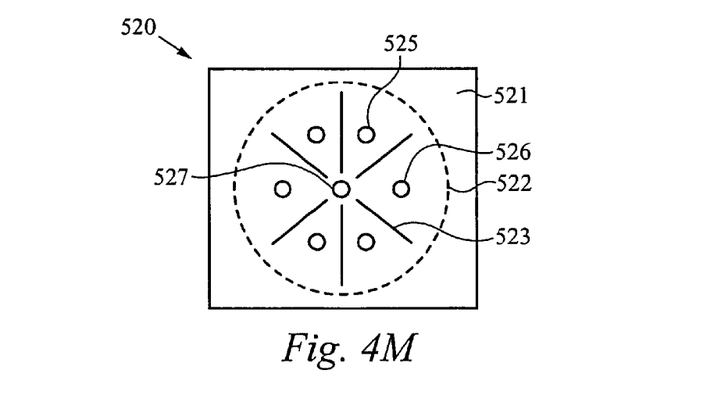

Referring now to FIG. 4M, a squeegee configuration 520, in accordance with the embodiments of the invention, comprises a plurality of squeegee segments 523 protruding form a support surface 521 and extending radially outward from a center 527 of a circle, as indicated by the dotted line 522. The squeegee segments can be surrounded or flanked by bristle, bristle sections and/or nodules 525 and 526. Preferably, the bristle, bristle sections and/nodules 525 and 526 are configured to move and contact a working surface (not shown) simultaneously with the top wiping edges of the squeegee segments 523.

Figure 5A:
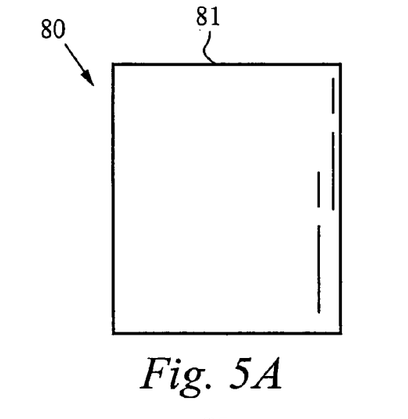
FIGS. 5A-F show several shaped or contoured squeegee edges, in accordance with the embodiments of the invention.
Figure 5B:
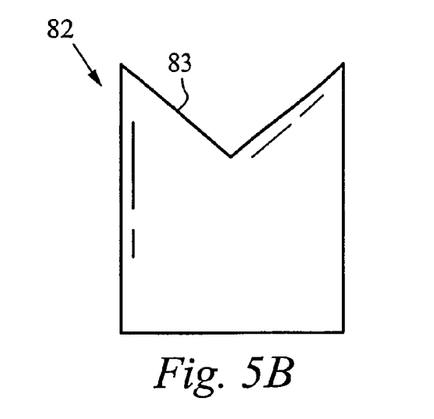
Figure 5C:
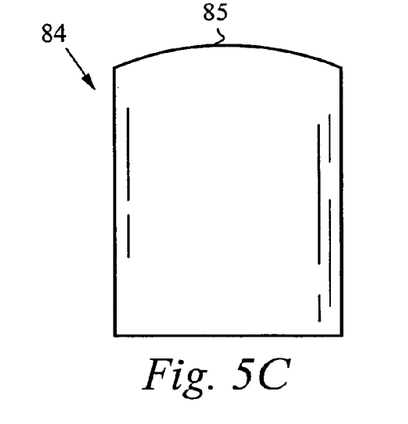
Figure 5D:
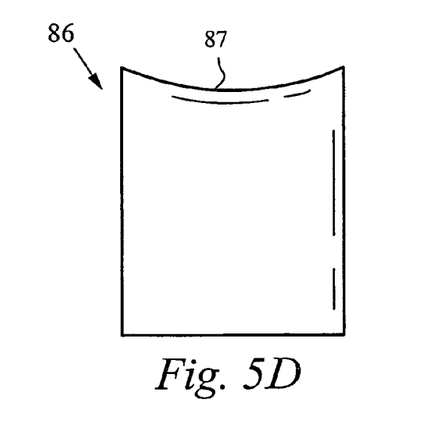
Figure 5E:
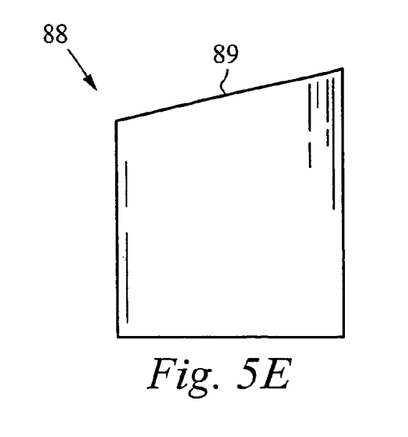
Figure 5F:
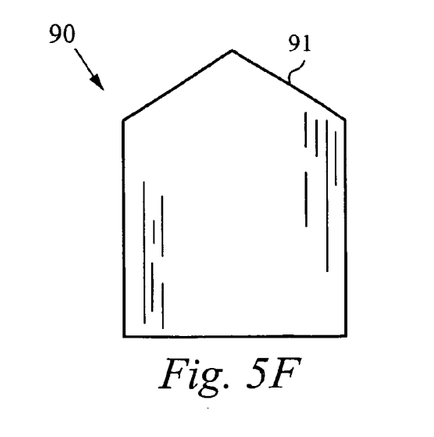

FIGS. 5A-F illustrate several shaped squeegee segments and/or partial structure or squeegee elements, used in the present invention. FIG. 5A shows a squeegee segment 80 with a planar contact edge 81; FIG. 5B shows a squeegee segment 82 with a V-shaped or notched contact edge 83; FIG. 5C shows a squeegee segment 84 with a curve convex contoured contact edge 85; FIG. 5D shows a squeegee segment 86 with a concave contoured contact edge 87; FIG. 5E shows a squeegee segment 88 with a diagonally contoured contact edge 89; and FIG. 5F shows a squeegee segment 90 with a pointed contact edge 91. The shaped squeegee segments described above can be combined in any number of ways to provide elongated squeegee wiping edges used in the oral cleaning device, system and method of the present invention.

Figure 6A:
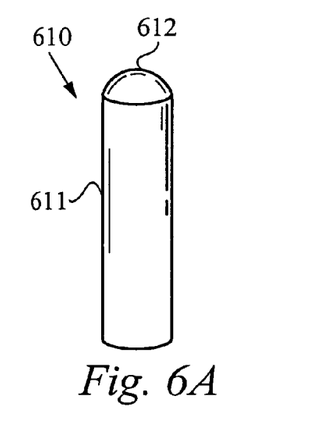
FIGS. 6A-H show nodule structures, in accordance with the embodiments of the invention.
Figure 6B:
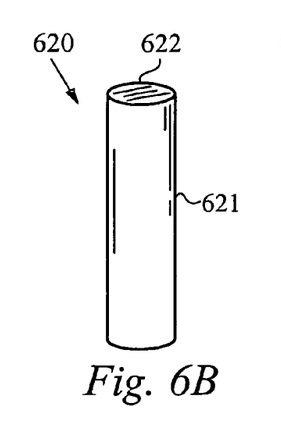
Figure 6C:
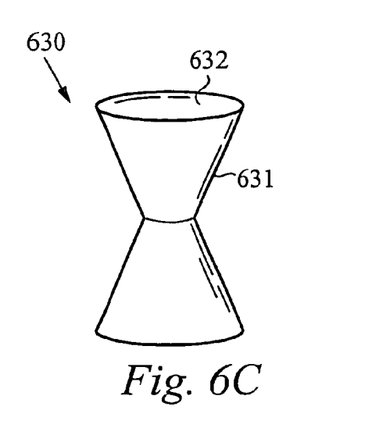
Figure 6D:
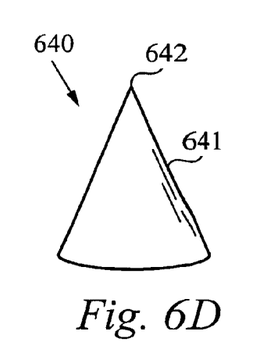
Figure 6E:
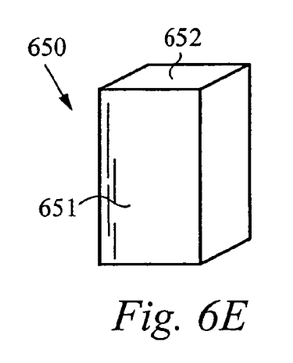
Figure 6F:
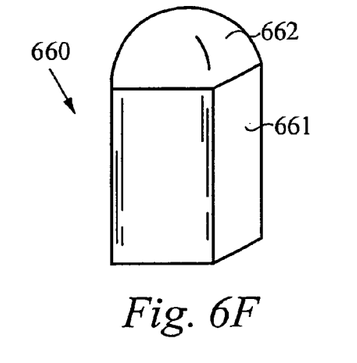
Figure 6G:
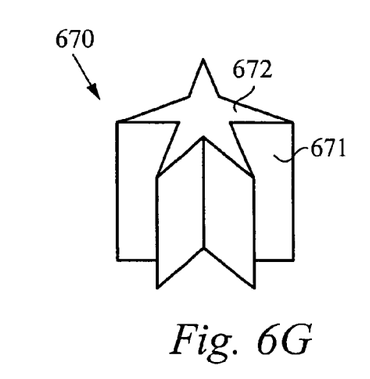
Figure 6H:
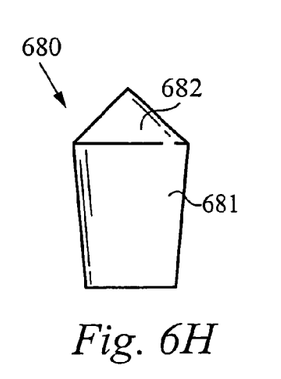

FIGS. 6A-H illustrate several symmetrical nodule structure geometries that are useful in contact devices of the present invention. FIG. 6A shows a nodule 610 with cylindrical protruding walls 611 and a rounded tip portion 612; FIG. 6B shows a nodule 620 with cylindrical protruding walls 621 and a flat top 622; FIG. 6C shows a nodule 630 with contoured protruding walls 631 and a flat top 632; FIG. 6D shows a pointed nodule 660 with tapered protruding walls 641 and a tip 642; FIG. 6E shows a rectangular nodule 650 with planar walls 651 and a flat top 652; FIG. 6F shows a nodule 660 with planar walls 661 and a rounded tip portion 662; FIG. 6G shows a star shaped nodule 670 with protruding walls 671 and a star-shaped top 672; and FIG. 6H shows a triangular nodule 680 with protruding walls 681 and triangular-shaped top 682.

Figure 7A:
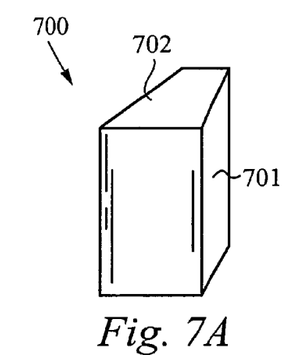
FIGS. 7A-G show alternative nodule structures, in accordance with the embodiments of the invention.
Figure 7B:
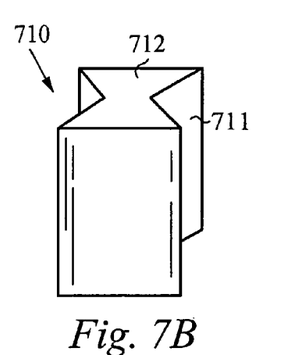
Figure 7C:
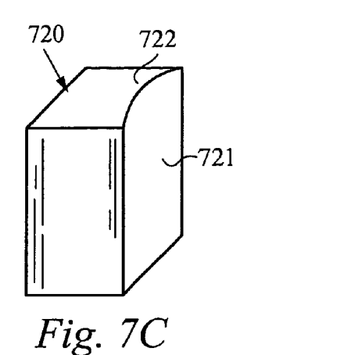
Figure 7D:
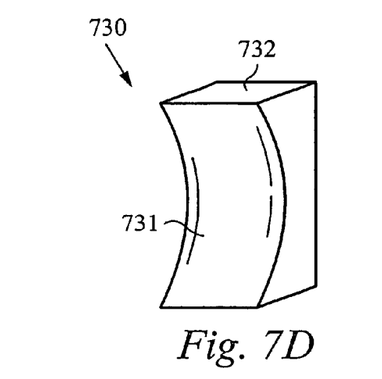
Figure 7E:
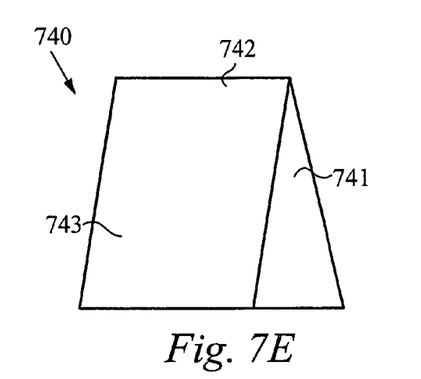
Figure 7F:
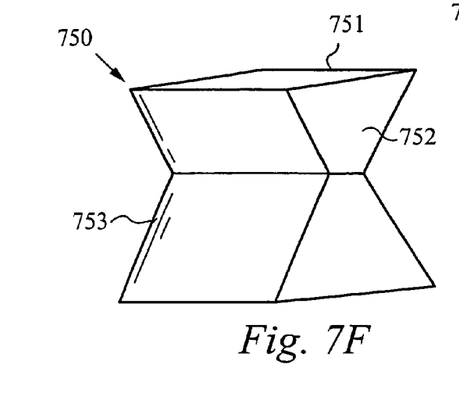
Figure 7G:
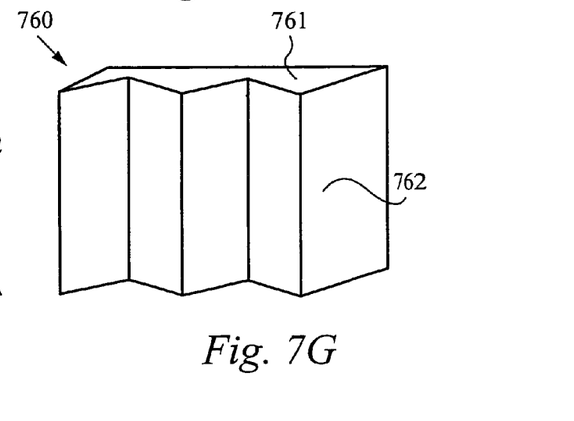

FIGS. 7A-G illustrate several asymmetrical nodule structure geometries that are useful in contact device of the present invention. FIG. 7A shows a wedge-shaped nodule 700 with protruding walls 701 and a top 702; FIG. 7B shows a nodule 710 with contoured walls 711 and a bow-tie shaped top 712; FIG. 7C shows a curved nodule 720 with protruding walls 721 (curved in the elongation direction) and a flat top 722; FIG. 7D shows a curved nodule 730 with protruding walls 731 (curved in the protruding direction) and a top 732; FIG. 7E shows a wedge shaped nodule 740 with tapered walls 743, triangular walls 741 and an edge 742; FIG. 7F shows a nodule 750 with grooved walls 753, bow-tie shaped walls 752 and a flat top 751; and FIG. 7G shows a nodule 760 with contoured walls 762 and a top 761. It will be clear to one skilled in the art that any number of symmetric and asymmetric nodule geometries and combinations thereof are useful in the contact device of the instant invention. Further descriptions of nodule structures and their applications are described in U.S. patent application Ser. No. 09/957,302, filed Sep. 19, 2001 and titled "DEVICE WITH MULTI-STRUCTURAL CONTACT ELEMENTS", now U.S. Pat. No. 6,859,767, referenced previously.

Figure 8:
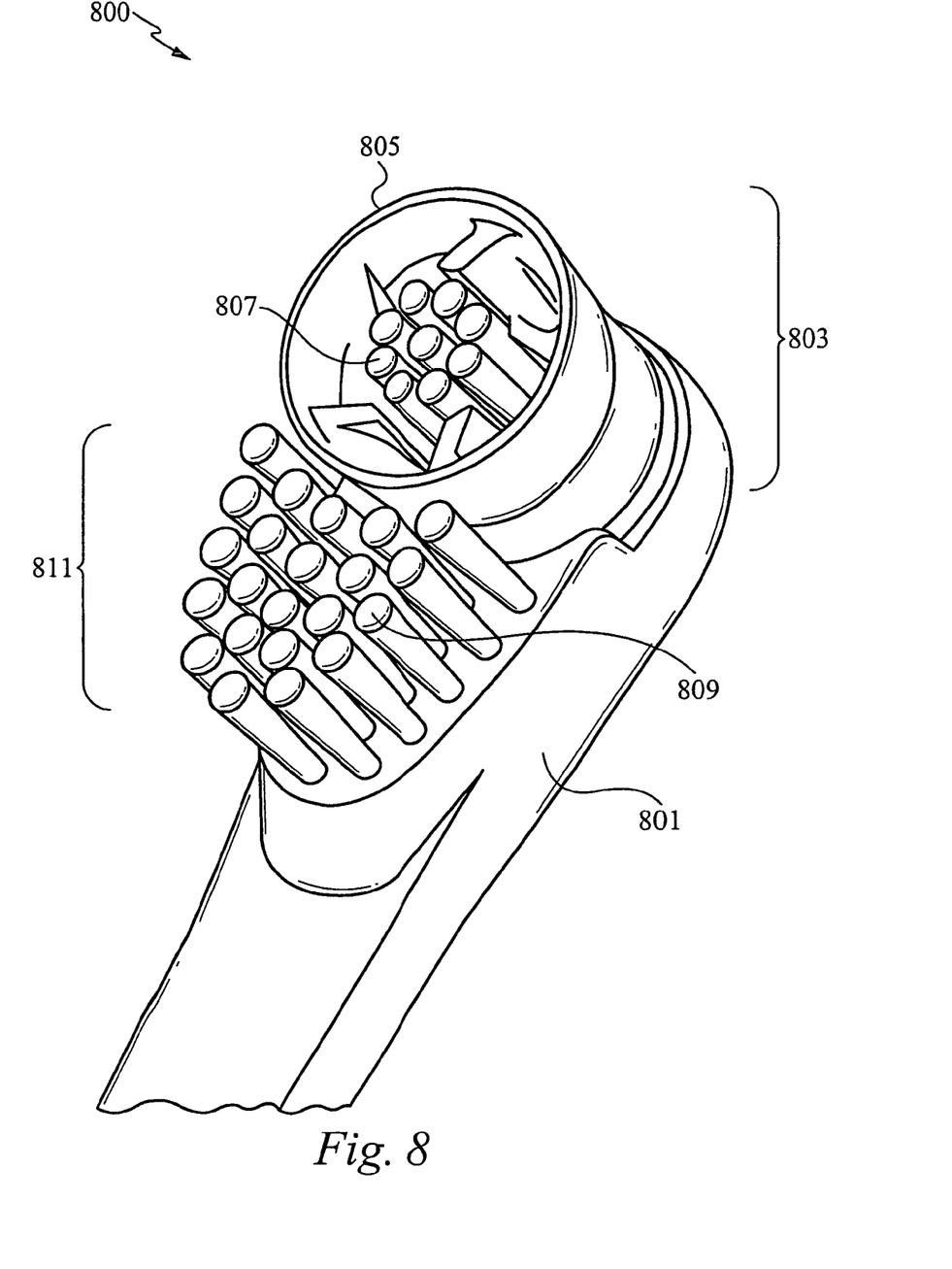
FIG. 8 shows a perspective view of a power head of an oral-care cleaning apparatus, in accordance with the embodiments of the invention.

FIG. 8 shows an oral-care cleaning head 800, in accordance with a preferred embodiment of the invention. The oral-care cleaning head 800 comprises a support structure 801 for supporting a first region 811 and a second region 803. The first region 811 comprises bristle tufts 809 for wiping the surfaces of gums and teeth. The second region 803 comprises a cup-shaped squeegee element 805 that includes a continuous squeegee segment encircling a portion of the second region 803 and squeegee fins protruding from an inner wall of the continuous squeegee segment. The continuous squeegee segment preferably encircles bristle tufts 807 that protrude from the second region for wiping surfaces of teeth and gums.

The first region 811 can be configured to remain stationary or move in any number of ways, as described above, while cleaning teeth and gums. Preferably the cup-shaped squeegee element 805 and the bristle tufts 807 of the second region 803 are configured to oscillate and/or rotate while cleaning teeth and/or gums. The oral-care cleaning head 800, described above is most preferably configured to detachably couple to a power handle, such as described with reference to FIG. 2.

It will be clear to one skilled in the art from the description above that top wiping edges and side wiping edges of the squeegee element and segments described can be contoured, corrugated, curved, pointed, angled, tapered or otherwise textured. While embodiments have been described with bristles, bristles are not required. Further, any number of the features described above can be combined in different ways to provide other squeegee configurations that are considered to be within the scope of the invention. It is also understood that an abrasive material can be integral with the squeegee segments or attached to the walls or edges of squeegees as required for the application at hand. Further, it is understood that the squeegee configurations, in accordance with the embodiments of the invention, can include absorbent elements, such as sponge elements, and abrasive elements, such as scouring elements that are separate from the squeegee segments. Also, walls of squeegee segments, while generally shown as uniform herein, can vary in thickness in either an elongated direction, in a protruding direction or both. Accordingly, the proceeding preferred embodiments of the invention are set forth without any loss of generality to, and without imposing limitations upon, the claimed invention.

The invention claimed is:

1. A device comprising a cleaning head, the cleaning head comprising
   a) a support structure;
   b) a plurality of squeegee segments protruding upward from a surface of the support structure, the squeegee segments each comprising two terminus ends that are inside edges and outside edges, wherein the plurality of squeegee segments extend radially outward from the inside edges to the outside edges along the surface of the support structure and, wherein the outside edges define an outside periphery and the inside edges define an inside periphery; and
   c) bristles that protrude from the surface of the support structure at locations between elongated squeegee walls of adjacent pairs of the plurality of squeegee segments.

2. The device of claim 1, wherein the support structure is configured to automatically move and thus automatically move the plurality of squeegee segments and the bristles together as a unit.

3. The device of claim 2, wherein the support surface is configured to vibrate, rotate or oscillate.

4. The device of claim 2, further comprising a motorized handle configured to detachably couple the cleaning head.

5. The device of claim 1, further comprising bristles that protrude from a center location within the inside periphery on the surface of the support structure.

6. The device of claim 1, wherein portions of the plurality of squeegee segments are corrugated, rounded, angled or pointed.

7. The device of claim 1, further comprising nodules protruding from the surface of the support structure.

8. The device of claim 7, wherein the nodules are corrugated, rounded, angled or pointed.

9. A device comprising a plurality of squeegee segments with substantially linear top wiping edges and two terminus ends that are inside edges and outside edges, wherein the substantially linear top wiping edges extend radially outward along a support surface with the outside edges defining a substantially circular outside periphery and the inside edges defining a substantially circular inside periphery, the device further comprising bristles protruding from the support surface between substantially linear walls of adjacent pairs of the squeegee segments.

* * * * *